United States Patent [19]

Nara et al.

[11] 4,097,428
[45] Jun. 27, 1978

[54] FORTIMICIN C AND PROCESS FOR PRODUCTION THEREOF

[75] Inventors: Takashi Nara, Tokyo; Ryo Okachi; Mitsuyoshi Yamamoto, both of Machida; Yasuki Mori, Kawasaki; Moriyuki Sato, Machida; Masahiro Sugimoto; Yoshiaki Shimizu, both of Shizuoka, all of Japan

[73] Assignee: Abbott Laboratories, North Chicago, Ill.

[21] Appl. No.: 800,925

[22] Filed: May 26, 1977

Related U.S. Application Data

[62] Division of Ser. No. 708,681, Jul. 26, 1976, Pat. No. 4,048,015.

[30] Foreign Application Priority Data

Aug. 1, 1975   Japan ................................. 50-93182

[51] Int. Cl.$^2$ ............................................ C07D 309/22
[52] U.S. Cl. ............................................... 260/345.9 R
[58] Field of Search .................................. 260/345.9 R

[56] References Cited

U.S. PATENT DOCUMENTS

| 3,931,400 | 1/1976 | Nara et al. | 424/118 |
| 3,976,768 | 8/1976 | Nara et al. | 424/118 |

*Primary Examiner*—Nicky Chan
*Attorney, Agent, or Firm*—Fitzpatrick, Cella, Harper & Scinto

[57] ABSTRACT

A new antibiotic, Fortimicin C, is produced by fermentation of a microorganism belonging to the genus Micromonospora. The antibiotic is accumulated in the culture medium and is isolated therefrom.

2 Claims, 3 Drawing Figures

FORTIMICIN C AND PROCESS FOR PRODUCTION THEREOF

This is a division of application Ser. No. 708,681, filed July 26, 1976, now U.S. Pat. No. 4,048,015.

RELATED APPLICATIONS

The present invention is related generally to the inventions disclosed in U.S. Pat. No. 3,931,400 issued Jan. 6, 1976 for Fortimicin B and Process For Production Thereof, and U.S. Pat. No. 3,976,768 issued Aug. 24, 1976 for Fortimicin A and Process For Production Thereof.

BACKGROUND OF THE INVENTION

The present invention relates to a new composition of matter having antibacterial properties, Fortimicin C. The present invention also pertains to the production of Fortimicin C by culturing a Fortimicin C producing microorganism belonging to the genus Micromonospora in a nutrient medium until antibacterial activity is detected in the culture liquor and then isolating the active substance therefrom.

Antibiotics which exhibit activity against a broad spectrum of bacteria are always in demand. To this end, it has been found that when a strain of Micromonospora (hereinafter sometimes referred to as the MK-70 strain) isolated from the soil of the paddy field in Hiroshima Prefecture, Japan is cultured in a nutrient medium, several antibiotic substances are produced in the culture liquor. Among the active substances, two antibiotics, namely Fortimicin B and A (which are respectively the subjects of the U.S. patent and patent application referred to above) were liberated. It has now been discovered that a third active substance is liberated by the MK-70 strain, and this substance has been named Fortimicin C. A study of the chemical, physical and biological properties of this substance indicates that the composition of matter is a new antibiotic.

SUMMARY OF THE INVENTION

In accordance with the present invention, a novel antibiotic, Fortimicin C, is produced by fermentation of a microorganism belonging to the genus Micromonospora, which is capable of producing the antibiotic, in a nutrient medium until substantial antibacterial activity is detected in the culture liquor. At the completion of culturing, the active fraction containing Fortimicin C is isolated from the liquor by known means such as by ion exchange resin treatment.

Fortimicin C exhibits a broad antibacterial spectrum and is, therefore, useful to clean and sterilize laboratory glassware and surgical instruments, and may also be used in combination with soaps, detergents and wash solutions for sanitation purposes.

Included in the composition of matter aspect of the invention are the pharmaceutically acceptable acid addition salts of Fortimicin C including the mineral acid addition salts such as hydrochloride, hydrobromide, hydroiodide, sulfate, sulfamate and phosphate and the organic addition salts such as the maleate, acetate, citrate, oxalate, succinate, benzoate, tartrate, fumarate, malate, mandelate, ascorbate and the like.

DESCRIPTION OF THE INVENTION

Fortimicin C is a novel composition of matter having antibacterial properties. The composition of matter is believed to have the following structural formula:

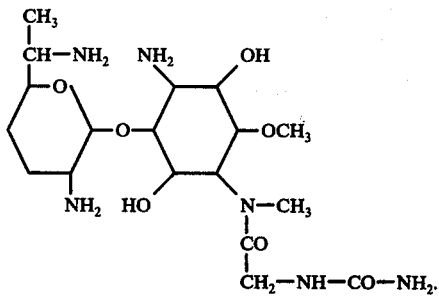

Fortimicin C is produced by fermentation of a microorganism belonging to the genus Micromonospora. Any strain belonging to the genus Micromonospora and capable of forming Fortimicin C in the culture liquor may be used. Examples of the preferred strains are *Micromonospora olivoasterospora* MK-70 (FERM-P No. 1560) (ATCC 21819), *Micromonospora olivoasterospora* MK-80 (FERM-P No. 2192) (ATCC 31010) and *Micromonospora olivoasterospora* Mm 744 (FERM-P No. 2193) (ATCC 31009). These strains have been deposited with the American Type Culture Collection, Rockville, Maryland, U.S.A. and with the Fermentation Research Institute, Agency of Industrial Science and Technology, Tokyo, Japan and have been accorded the accession numbers noted above.

The microbiological properties of these strains are described in U.S. Pat. No. 3,931,400, which description is expressly incorporated herein by reference.

As is the case with other strains of Actinomycetes, the microorganisms useful in carrying out the present invention can be mutated by artificial means such as ultraviolet irradiation, X-ray irradiation and use of various mutation inducing chemicals in known manner to enhance the production of metabolic products. Accordingly the present invention contemplates use of such mutants insofar as they have the ability to produce Fortimicin C.

Generally, conventional methods for culturing microorganisms of the Actinomycetes may be employed in the process of the present invention. Thus, various nutrient sources may be used for the culture medium. Appropriate carbon sources include glucose, starch, mannose, fructose, sucrose, molasses, etc. used either alone or in combination. Additionally, hydrocarbons, alcohols, organic acids, etc. may also be used depending upon the assimilability possessed by the particular microorganism employed. As inorganic and organic nitrogen sources, ammonium chloride, ammonium sulfate, urea, ammonium nitrate, sodium nitrate, etc. may be used either alone or in combination or natural nitrogen sources, such as peptone, meat extract, yeast extract, dry yeast, corn steep liquor, soybean powder, casamino acid, soluble vegetable protein, etc. are appropriate. If necessary, inorganic salts such as sodium chloride, potassium chloride, calcium carbonate, phosphates, etc. may be employed. Moreover, organic and inorganic materials which promote the growth of the particular strain and the production of Fortimicin C may be properly added to the medium.

A liquid culturing method, particularly a submerged stirring culturing method is most suitable for the process of the present invention. Culturing temperature is desirably 25°–40° C, and it is preferred to carry out culturing at around neutral pH. Usually, after 2 to 15 days of liquid culturing, Fortimicin C is formed and accumulated in the culture liquor. When the yield of the antibiotic in the culture liquor reaches a maximum, culturing is discontinued and the product is isolated and purified from the culture liquor after the microbial cells have been removed such as by filtration.

Isolation and purification of Fortimicin C from the culture filtrate is carried out according to the methods usually used for the isolation and purification of microbial metabolic products from the culture liquor.

Since Fortimicin C is basic and is readily soluble in water but poorly soluble in the ordinary organic solvents, the antibiotic can be purified by the methods usually used for the purification of so-called water-soluble basic antibiotics. More specifically, Fortimicin C can be purified by a proper combination of adsorption and desorption from cation exchange resins; cellulose column chromatography; adsorption and desorption using a column of Sephadex (trade name, produced by Pharmacia Fine Chemicals Inc., U.S.A.) LH-20; silica gel column chromatography and the like methods. For example, the cell-free culture filtrate is first adjusted to a pH 7.5 and then contacted with a cation exchange resin such as Amberlite (trade name, produced by Rohm & Haas Co., U.S.A.) IRC-50 (ammonia form). After the resin is washed with water, elution is carried out with 0.5N aqueous ammonia. The active fractions are combined and concentrated under reduced pressure. The concentrate is then treated with an anion exchange resin such as Dowex (trade name, produced by Dow Chemical Co., U.S.A.) 1 × 2 (OH$^-$ form). The active fractions obtained by elution with water are combined and concentrated under reduced pressure to obtain a crude powder of active substances. The crude powder is then dissolved in water. The solution is adjusted to a pH of 5.0 with 2N sulfuric acid and then passed through a column packed with activated carbon. The active principles are adsorbed on the carbon. After washing the column with water to remove impurities, elution is carried out with 0.2N sulfuric acid to elute the active principles. The active fractions are then combined and passed through a column of an anion exchange resin such as Dowex 44 (OH$^-$ form) for neutralization. The effluent is then freeze-dried to obtain the free base of a complex of the active components.

The crude powder is then subjected to silica gel column chromatography using the lower layer of chloroform, isopropanol and aqueous ammonia (2:1:1) as a developer. The crude powder is suspended in the solvent and introduced to the column. Development is carried out with the same solvent at a flow rate of about 30 ml/hour. Initially, an active fraction previously identified as Fortimicin B is eluted out; and, after several trace components are eluted, the fraction previously identified as Fortimicin A is eluted out in large active fractions. Thereafter, elution is continued and Fortimicin C is eluted out in the next large active fractions.

The active fractions containing Fortimicin C are combined and concentrated under reduced pressure. The concentrate is freeze-dried to obtain a white powder which is the free base of Fortimicin C. The thus obtained preparate of Fortimicin C has a comparatively high purity. However, the preparate is sometimes contaminated with impurities and, in such a case, the sample is subjected to cellulose column chromatography. As the developer, a mixed solvent of n-butanol, pyridine, acetic acid and water (6:4:2:4) is used. The active fractions obtained by elution are combined and concentrated under reduced pressure to obtain a purified preparate of Fortimicin C.

When the impurity is a substance which shows a positive reaction with ninhydrin, column chromatography using carboxymethylcellulose is also effective. More specifically, in this case, a solution of the crude powder containing Fortimicin C is passed through a column packed with carboxymethylcellulose (ammonia form). The active principles are adsorbed on the carboxymethylcellulose. Then, the column is thoroughly washed with water to elute most of the pigments and inorganic salts therefrom. Thereafter, elution is carried out with 0.2N ammonium bicarbonate to elute the active principles. Fractions containing Fortimicin C are combined and freeze-dried to obtain a purified preparate.

During the above-described purification procedures, the fractions are checked by ascending paper chromatography using Whatman No. 1 filter paper. As the developer, the lower layer of chloroform, methanol and 17% aqueous ammonia (2:1:1) is used and development is carried out at room temperature for 6–15 hours. The Rf value of Fortimicin C on the paper chromatogram is about 0.18.

Fortimicin C, in its free base form, is a white, basic powder. The elementary analytical values as found are C = 44.84%, H = 8.19%, N = 17.36% and O = 29.61%. The molecular weight is 448 (calculated based on the results obtained by high resolution mass spectrometry) and the empirical formula is considered to be $C_{18}H_{36}N_6O_7$. The elementary analytical values as calculated are C = 44.62%, H = 8.32%, N = 17.34% and O = 29.72%. Fortimicin C has a melting point of 160° C (decomposition).

The ultraviolet absorption spectrum of an aqueous solution of Fortimicin C does not show characteristic maximum absorption between 220 and 360 mμ but only shows terminal absorption.

The specific rotation of the free base of Fortimicin C is $[\alpha]_D^{25} = +84°$ (c = 0.1, $H_2O$).

FIG. 1 illustrates the infrared absorption spectrum (measured in KBr) of Fortimicin C. Fortimicin C shows peaks at the following wavenumber (cm$^{-1}$):

3400, 2900, 1625, 1570, 1450, 1350, 1100, 1030

Figure 1:
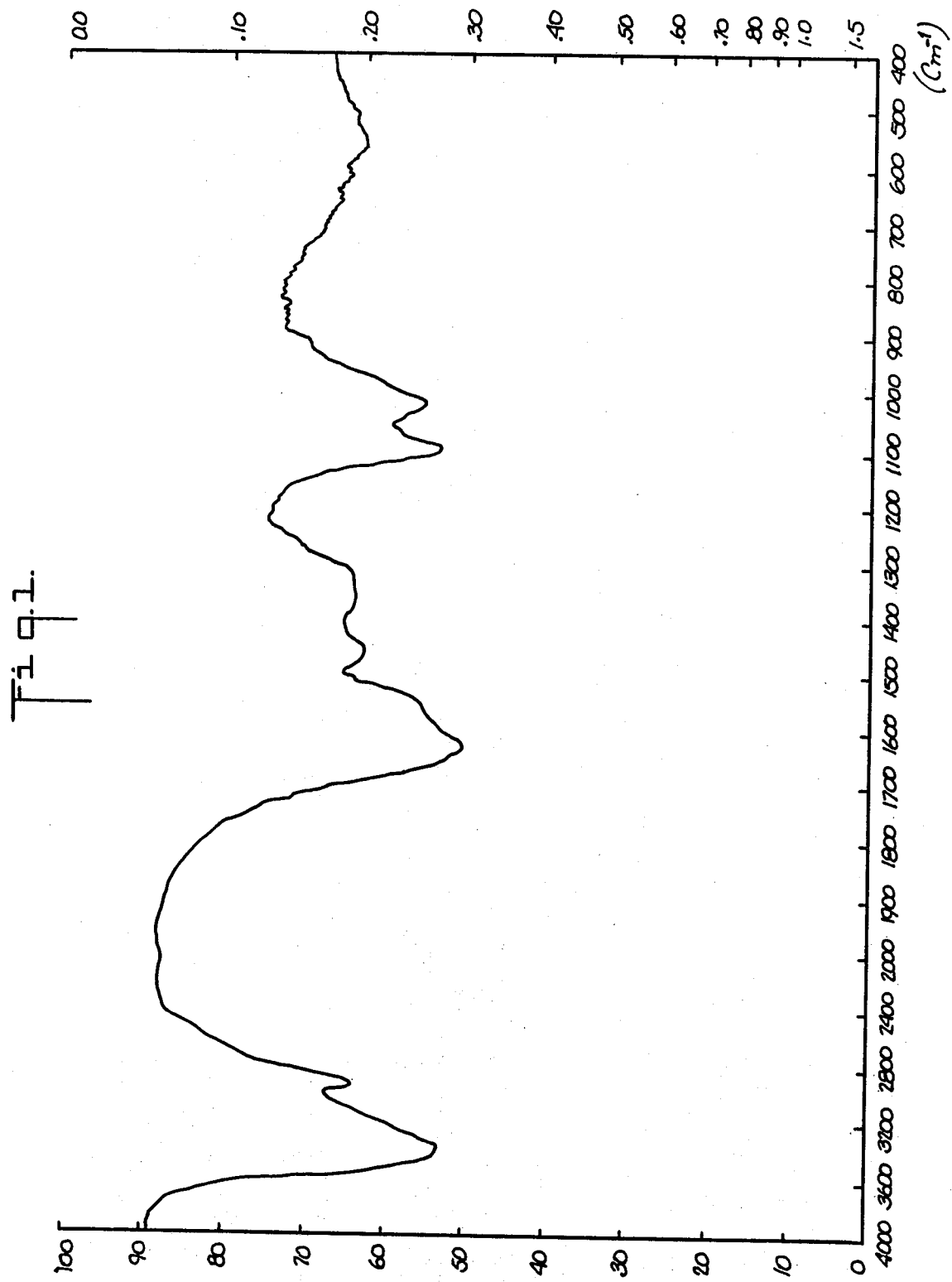
Figure 2:
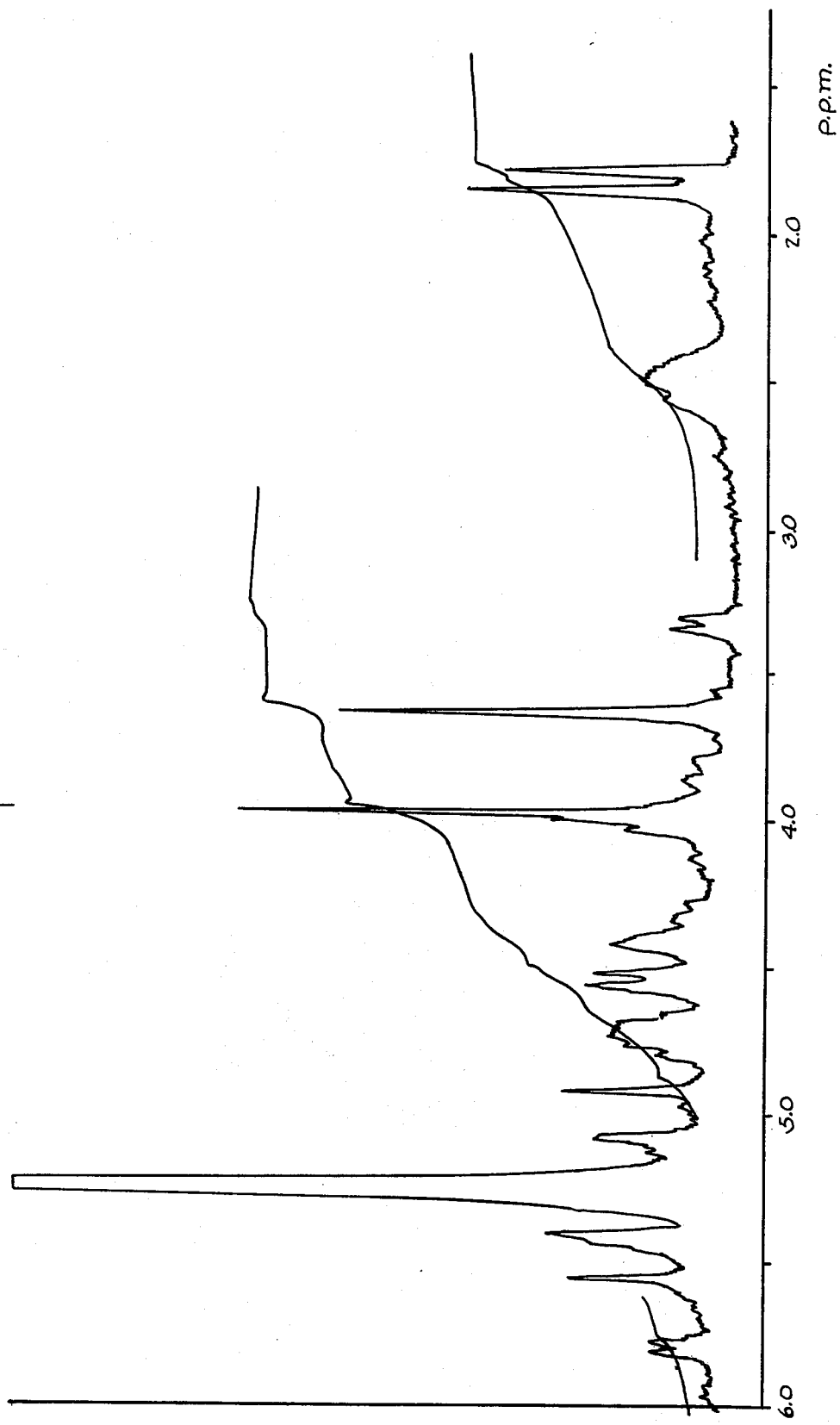
FIG. 2 illustrates the PMR spectrum of Fortimicin C hydrochloride ($D_2O$ solution) wherein the chemical shifts are reported in ppm (δ) downfield from external TMS.
Figure 3:
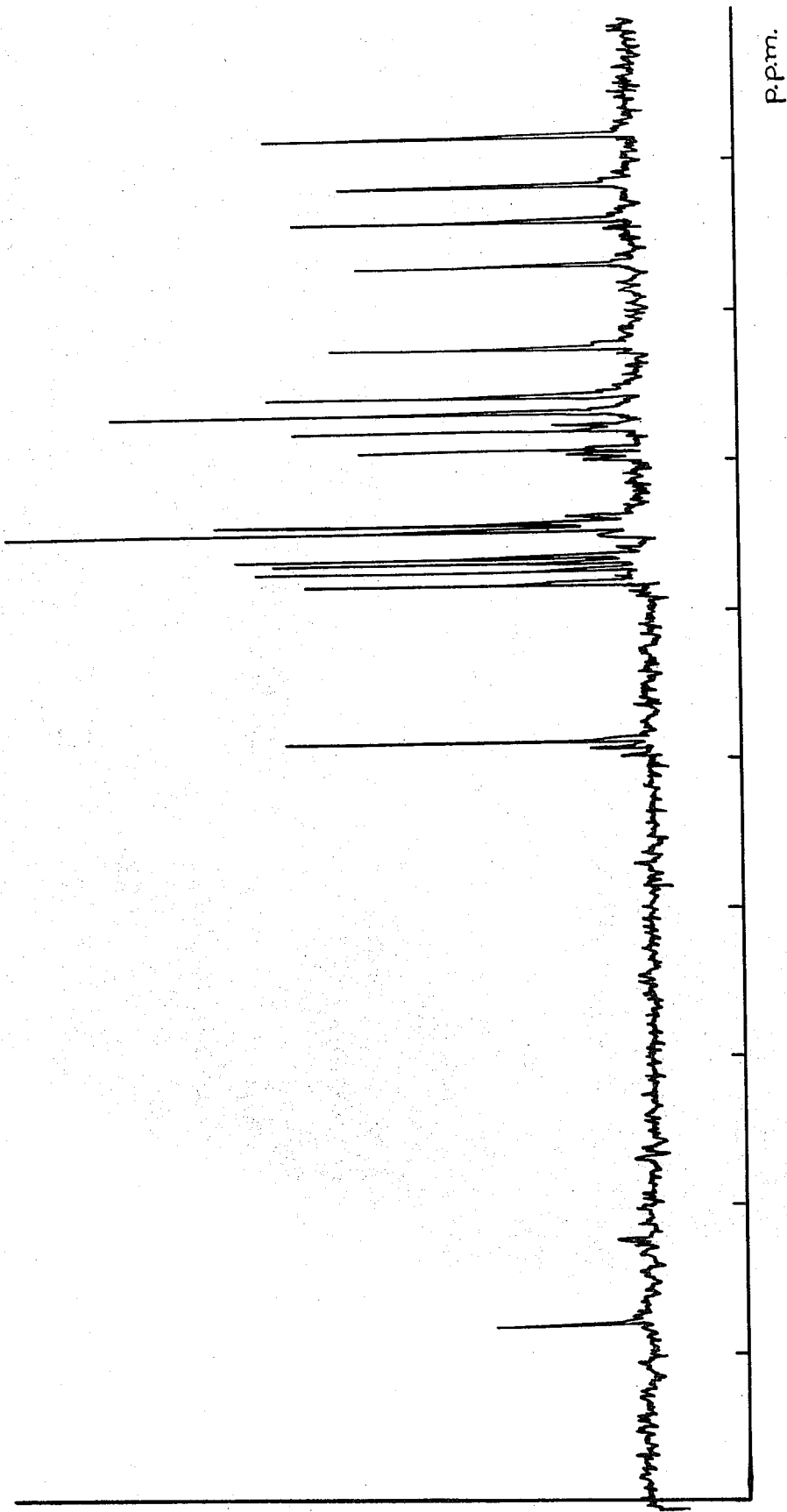
FIG. 3 illustrates the CMR spectrum of Fortimicin C hydrochloride ($D_2O$ solution) wherein the chemical shifts are reported in ppm downfield from TMS but are measured from internal dioxane 67.4 ppm.

Based upon the foregoing analyses, the composition of matter is considered to have the following structure:

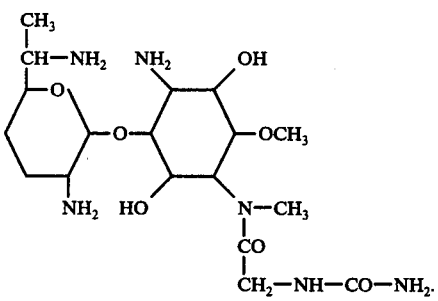

In color reactions, Fortimicin C shows positive reaction in ninhydrin test and potassium permanganate test and negative reaction in Elson-Morgan's test and biuret test.

The free base of Fortimicin C is readily soluble in water, soluble in methanol and slightly soluble in ethanol and acetone but is insoluble in organic solvents such as chloroform, benzene, ethyl acetate, butyl acetate, ethyl ether, butanol, petroleum ether, n-hexane, and the like.

The Rf values of Fortimicin C in paper chromatography and thin layer chromatography using various developers are shown in the following Tables 1, 2 and 3. For comparison, the Rf values of antibiotics which are similar to Fortimicin C are also given.

Table 1
The Rf values of Fortimicin C in ascending paper chromatography (at 28° C)

| Developer | Rf value | Period of development (hour) |
| --- | --- | --- |
| 20% Ammonium chloride | 0.96 | 3 |
| Water-saturated n-butanol | 0.00 | 15 |
| n-Butanol:acetic acid:water (3 : 1 : 1) | 0.06 | 15 |
| Water-saturated ethyl acetate | 0.00 | 4 |
| Water-saturated n-butanol containing 2% (W/V) p-toluene sulfonic acid and 2% (V/V) piperidine | 0.04 | 15 |

Table 2
The Rf values of Fortimicin C gentamicin complex, gentamicin $C_{1a}$ and sisomicin in silica gel thin layer chromatography (at room temperature; after three hours of development)

| Developer* | Antibiotics | Rf value |
| --- | --- | --- |
| I | Fortimicin C | 0.74 |
| " | Gentamicin complex | 0.71 |
| " | Gentamicin $C_{1a}$ | 0.71 |
| " | Sisomicin | 0.71 |
| II | Fortimicin C | 0.40 |
| " | Gentamicin complex | 0.06–0.16 |
| " | Gentamicin $C_{1a}$ | 0.16 |
| " | Sisomicin | 0.18 |

*Developer I:
The upper layer of chloroform, methanol and 17% aqueous ammonia (2:1:1 by volume).
Developer II:
10% ammonium acetate and methanol (1:1 by volume).

Table 3
The Rf values of various antibiotics in ascending paper chromatography using the lower layer of chloroform, methanol and 17% aqueous ammonia (2:1:1) as the developer (at room temperature; after 12 hours of development).

| Antibiotics | Rf value |
| --- | --- |
| Streptomycin A | 0.02 |
| Streptomycin B | 0.00 |
| Bluensomycin | 0.01 |

Table 3-continued
The Rf values of various antibiotics in ascending paper chromatography using the lower layer of chloroform, methanol and 17% aqueous ammonia (2:1:1) as the developer (at room temperature; after 12 hours of development).

| Antibiotics | Rf value |
| --- | --- |
| Ribostamycin | 0.00 |
| Lividomycin A | 0.00 |
| Lividomycin B | 0.03 |
| Lividomycin D | 0.02 |
| Spectinomycin | 0.45 |
| Kasugamycin | 0.01 |
| Butirosine A | 0.00 |
| Butirosine B | 0.01 |
| Hygromycin B | 0.02 |
| Gentamicin A | 0.00 |
| Gentamicin B | 0.00 |
| Gentamicin $C_{1a}$ | 0.18 |
| Gentamicin $C_1$ | 0.59 |
| Gentamicin $C_2$ | 0.38 |
| Sisomicin | 0.18 |
| Neomycin A | 0.00 |
| Neomycin B | 0.03 |
| Antibiotic No. 460 | 0.01 |
| Neomycin C | 0.00 |
| Kanamycin A | 0.02 |
| Kanamycin B | 0.01 |
| Kanamycin C | 0.02 |
| Paromomycin | 0.00 |
| Nebramycin complex | 0.01 |
| Tobramycin | 0.02 |
| Apramycin | 0.02 |
| Nebramycin factor 4 | 0.01 |
| Nebramycin factor 5 | 0.00 |
| Myomycin | 0.00 |
| XK-62-2* | 0.49 |
| Fortimicin B | 0.65 |
| Fortimicin A | 0.37 |
| Fortimicin C | 0.18 |

*A new antibiotic disclosed in U.S. Pat. Application Serial No. 364,058, filed May 25, 1973.

The antibacterial spectra of Fortimicin C against various microorganisms determined by agar dilution method (pH 8) are given in the following Table 4.

Table 4

| Microorganism Tested | Minimum Inhibitory Concentration (γ/ml) |
| --- | --- |
| Bacillus subtilis No. 10707 | 0.16 |
| Staphylococcus aureus ATCC 6538P | 0.33 |
| Klebsiella pneumoniae ATCC 10031 | 0.66 |
| Escherichia coli ATCC 26 | 1.3 |
| Escherichia coli KY 8327 (resistant to kanamycin, gentamicin and tobramycin) | 1.3 |
| Pseudomonas aeruginosa BMH No. 1 | 5 |
| Pseudomonas aeruginosa KY 8510 (resistant to kanamycin, kanamycin B tobramycin, gentamicin $C_{1a}$ and ribostamycin) | 5 |
| Shigella sonnei ATCC 9290 | 2.6 |
| Salmonella typhosa ATCC 9992 | 0.66 |

As is apparent from the above, Fortimicin C exhibits a strong antibacterial activity against a wide range of Gram-positive and Gram-negative bacteria. Particularly, it is characteristic that the antibiotic is effective against certain strains of Escherichia coli which are resistant to kanamycin, gentamicin and tobramycin. It is, therefore, expected that Fortimicin C will be effective against various infections induced by the above-mentioned bacteria.

With such excellent antibacterial activities, Fortimicin C is applicable to medicinal purposes particularly as an antibacterial antibiotic.

A comparison of Fortimicin C with other antibiotics further illustrates its novelty. As water-soluble, basic antibiotics produced by microorganisms of the genus Micromonospora and having a broad range of antibacterial spectra, there are such antibiotics as the gentamicin complex [M. J. Weinstein et al.: Antimicrobial Agents and Chemotherapy, 1963, 1; D. J. Cooper et al.: J. Infect. Dis. 119, 342, (1969); and J. A. Waitz et al.: Antimicrob. Ag. Chemoth. 2, 464, (1972)], antibiotic No. 460 (Japanese Patent Publication No. 16153/71), sisomicin [M. J. Weinstein et al.: J. Antibiotics, 23, 551, 555, 559, (1970)], XK-62-2 (U.S. patent application Ser. No. 364,058, filed May 25, 1973), Fortimicin B (U.S. Pat. No. 3,931,400) and Fortimicin A (U.S. patent application Ser. No. 490,668, filed July 22, 1974) etc. With regard to the gentamicin complex, as shown in the above Table 3, gentamicin A, B, $C_2$ and $C_1$ components show Rf values of 0.00, 0.00, 0.38 and 0.59, respectively in paper chromatography. On the other hand, in the same paper chromatography, the Rf value of Fortimicin C is 0.18. Thus, Fortimicin C is clearly different from these gentamicin components. In the paper chromatography reported in Table 3, Fortimicin C shows the same Rf value (0.18) as that of gentamicin $C_{1a}$ (0.18); however, in silica gel thin layer chromatography (Table 2) using the developer II, Fortimicin C (Rf value: 0.40) is clearly distinguished from gentamicin $C_{1a}$ (Rf value: 0.16). When compared with antibiotic No.460, XK-62-2 and Fortimicin B, it is apparent that Fortimicin C is different from these antibiotics since the Rf values (Table 3) of antibiotic No. 460, XK-62-2 and Fortimicin B are respectively 0.01, 0.49 and 0.65, whereas the Rf value of Fortimicin C is 0.18. In paper chromatography, sisomicin also has a Rf value of 0.18 but in the silica gel thin layer chromatography (Table 2) using the developer II, Fortimicin C (Rf value: 0.40) and sisomicin (Rf value: 0.18) are clearly distinguished from each other.

As water-soluble, basic antibiotics produced by Actinomycetes other than those of the genus Micromonospora and having a broad range of antibacterial spectrum, there are such antibiotics as streptomycin, ribostamycin, lividomycin, spectinomycin, kasugamicin, neomycin, kanamycin, nebramycin and paromomycin. Fortimicin C has been found to be greatly different from any of these antibiotics in physicochemical properties. Moreover, as is apparent from Table 3, Fortimicin C is quite different from these antibiotics in Rf value.

Practice of certain specific embodiments of the invention is illustrated by the following representative examples.

EXAMPLE 1

In this example, *Micromonospora olivoasterospora* MK-70 (ATCC 21819) (FERM-P No. 1560) is used as a seed strain and a medium comprising 2 g/dl glucose, 0.5 g/dl peptone, 0.5 g/dl yeast extract and 0.1 g/dl calcium carbonate (pH 7.5 before sterilization) is used as a first seed medium. One loopful of the seed strain is inoculated into 10 ml portions of the first seed medium in 50 ml-large test tubes and cultured with shaking at 30° C for 5 days. Then, 10 ml of the thus prepared first seed culture is inoculated into 30 ml portions of a second seed medium in 250 ml-Erlenmeyer flasks. The second seed medium has the same composition as that of the first seed medium. The second seed culturing is carried out with shaking at 30° C for 2 days.

Then, 30 ml of the second seed culture is inoculated into 300 ml portions of a third seed medium in 2 l-Erlenmeyer flasks provided with baffles. The third seed medium has the same composition as that of the first seed medium. The third seed culturing is carried out with shaking at 30° C for 2 days and 1.5 l of the third seed culture (corresponding to 5 flasks) is inoculated into 15 l of a fourth seed medium in a 30 l-stainless steel jar fermenter. The fourth seed medium has the same composition as that of the first seed medium. Culturing in the jar fermenter is carried out with aeration and stirring (revolution: 350 r.p.m.; aeration: 15 l/min.) at 37° C for 2 days. Thereafter, 15 l of the fourth seed culture is inoculated into 150 l of a main fermentation medium in a 300 l-fermenter. The main fermentation medium has the following composition.

| | | |
|---|---|---|
| Soluble starch | 4 | g/dl |
| Soybean meal | 2 | g/dl |
| Corn steep liquor | 1 | g/dl |
| $K_2HPO_4$ | 0.05 | g/dl |
| $MgSO_4 \cdot 7H_2O$ | 0.05 | g/dl |
| KCl | 0.03 | g/dl |
| $CaCO_3$ | 0.1 | g/dl |
| (pH 7.5 before sterilization) | | |

Culturing in the fermenter is carried out with aeration and stirring (revolution: 150 r.p.m.; aeration: 80 l/min.) at 37° C for 4 days.

After the completion of culturing, the culture liquor is adjusted to pH 2.5 with concentrated sulfuric acid and stirred for 30 minutes. Thereafter, about 7 kg of a filter aid, Radiolite No. 600 (product of Showa Kagaku Kogyo Co., Ltd.) is added thereto and the microbial cells are removed by filtration. The filtrate is adjusted to pH 7.5 by the addition of 6N sodium hydroxide, and then passed through a column packed with about 20 l of a cation exchange resin, Amberlite IRC-50 (ammonia form). The effluent is discarded. The active principles are adsorbed on the resin. After the resin is washed with water, elution of the active principles is carried out with 0.5N aqueous ammonia. The activity of the eluate is determined by a paper disc method using an agar plate of *Bacillus subtilis* No. 10707. Fractions showing an activity are combined and concentrated under reduced pressure to about 1 l. The concentrate is passed through a column packed with 500 ml of an anion exchange resin, Dowex 1 × 2 ($OH^-$ form) and then about 2 l of water is passed through the column. In this matter, impurities are removed and the active principles are eluted with water. The active fractions are combined and concentrated under reduced pressure to about 100 ml. The concentrate is then passed through a column packed with about 50 ml of active carbon powder. The active principles are adsorbed on the active carbon. The column is washed with water and the effluent and washing water are discarded. Then, elution is carried out with 0.2N sulfuric acid. The eluate is subjected to determination of the activity by the paper disc method using *Bacillus subtilis*, and the active fractions are combined and passed through a column of Dowex 44 ($OH^-$ form) and elution of the active principles is carried out with water. The active fractions are combined and concentrated to about 50 ml. The thus obtained concentrate is freeze-dried to obtain a crude powder of the Fortimicin complex. The yield of the crude powder is 31 g and the activity is 570 unit/mg (activity of 1 mg of the pure preparate corresponds to 1,000 units).

To isolate and purify Fortimicin C, about 500 ml of silica gel is packed into a glass column and 10 g of the crude powder obtained in the above step is charged over the silica gel to form a uniform, thin layer. The silica gel is previously suspended in a solvent comprising lower layer of chloroform, isopropanol and 17% aqueous ammonia (2:1:1 by volume) and packed in the column as a tight, uniform layer. Thereafter, the column is thoroughly washed with the same solvent. After the crude powder is charged, the same solvent is poured gradually into the column from the top and thereafter elution is carried out continuously at a flow rate of about 50 ml/hour. The eluate is recovered in 20 ml fractions and each of the fractions is subjected to determination of the activity by the paper disc method. First, Fortimicin B is eluted followed by Fortimicin A. The elution is continued and then Fortimicin C is eluted out. The active fractions are subjected to paper chromatography and the fractions containing a component corresponding to Fortimicin C are combined and concentrated under reduced pressure to remove the solvent. The residue is dissolved in a small amount of water and the solution is freeze-dried to obtain about 0.9 g of a purified preparate of the free base of Fortimicin C. The product exhibits an activity of about 980 unit/mg.

EXAMPLE 2

In this example, the same seed strain and first through fourth seed culturing of Example 1 are repeated. However, a fermentation medium having the following composition is used for the main fermentation step:

| | | |
|---|---|---|
| Soluble starch | 4 | g/dl |
| Ebios (dry yeast powder) | 3 | g/dl |
| $K_2HPO_4$ | 0.05 | g/dl |
| $MgSO_4 \cdot 7H_2O$ | 0.05 | g/dl |
| KCl | 0.03 | g/dl |
| $CaCO_3$ | 0.1 | g/dl |

Culturing and isolation is carried out under the same conditions as described in Example 1 whereby about 63 g of a crude powder of the Fortimicin complex exhibiting an activity of about 650 unit/mg is obtained. Then, 50 g of the crude powder is subjected to purification according to the method described in Example 1 to obtain about 7 g of Fortimicin C exhibiting an activity of about 850 unit/mg.

For further purification, the preparate is subjected to cellulose column chromatography. Specifically, about 500 ml of a cellulose powder such as AVICEL (product of Funakoshi Seiyaku K.K.) previously suspended in a solvent of n-butanol, acetic acid, pyridine and water (6:2:4:4) is packed in a glass column to form a tight, uniform layer. The column is then thoroughly washed with the same solvent. The preparate is then charged over the cellulose powder in the column in a thin layer and the same solvent is poured gradually into the column from the top and thereafter elution is carried out continuously at a flow rate of about 1 ml/min. The eluate is recovered in 10 ml fractions and each of the fractions is subjected to determination of the activity by the paper disc method. The active fractions are combined and concentrated under reduced pressure to remove the solvent and the residue is dissolved in a small amount of water and freeze-dried. In such manner, about 3.5 g of a purified preparate of the free base of Fortimicin C exhibiting an activity of 950 unit/mg is obtained.

EXAMPLE 3

In this example, the same seed strain and first through fourth seed culturing of Example 1 are repeated. However, a main fermentation medium having the following composition is used:

| | | |
|---|---|---|
| Soluble starch | 4 | g/dl |
| Casamino acid (an acid hydrolyzate of casein, product of Difco Laboratories, U.S.A.) | 3 | g/dl |
| $K_2HPO_4$ | 0.05 | g/dl |
| $MgSO_4 \cdot 7H_2O$ | 0.05 | g/dl |
| KCl | 0.03 | g/dl |
| $CaCO_3$ | 0.1 | g/dl |

Culturing, isolation and purification of Fortimicin C are carried out in the same manner as in Example 1, whereby about 6.5 g of a purified preparate of Fortimicin C exhibiting an activity of about 980 unit/mg is obtained.

EXAMPLE 4

In this example, a culture liquor is obtained by carrying out culturing in the same manner as in Example 1. The culture liquor is then treated in the same manner as in Example 1 to obtain 3 g of a crude powder containing Fortimicin C. The crude powder is dissolved in 5 ml of water and passed through a column packed with about 200 ml of carboxymethylcellulose (ammonia form). Thereafter, about 1,000 ml of water is passed through the column whereby the active principles are adsorbed on the carboxymethylcellulose and most of the pigments and inorganic salts which are not adsorbed on the carboxymethylcellulose are eluted. Then, elution is carried out with 0.2M citric acid-phosphoric acid buffer (pH 3.0) (flow rate: about 50 ml/hour). The eluate is recovered in 10 ml fractions and each of the fractions is subjected to determination of the activity by the paper disc method. The active fractions are subjected to paper chromatography and fractions containing a component corresponding to Fortimicin C are combined and passed through a column of Amberlite CG-50 ($H^+$ form) whereby the active principles are adsorbed on the resin. After the resin is washed with water, elution is carried out with 0.5N hydrochloric acid. The active fractions are combined and passed through a column of Dowex 44 ($OH^-$ form) for neutralization. By freeze-drying the active fractions, about 350 mg of the free base of Fortimicin C is obtained which exhibits an activity of about 985 unit/mg.

EXAMPLE 5

In this example, *Micromonospora olivoasterospora* Mm 744, KY 11067 (FERM-P No. 2193, ATCC 31009) is used as a seed strain. The first through fourth seed culturing is carried out in the same manner as in Example 1 using a seed medium comprising 2 g/dl glucose, 0.5 g/dl peptone, 0.3 g/dl yeast extract and 0.1 g/dl calcium carbonate (pH 7.2 before sterilization). Then, 15 l of the fourth seed culture is inoculated into 150 l of a main fermentation medium in a 300 l-stainless steel fermenter. The main fermentation medium has the following composition:

| | | |
|---|---|---|
| Soluble starch | 2 | g/dl |
| Soybean meal | 0.5 | g/dl |
| Glucose | 2 | g/dl |
| Corn Steep liquor | 1 | g/dl |
| Yeast extract | 1 | g/dl |
| $K_2HPO_4$ | 0.05 | g/dl |
| $MgSO_4 \cdot 7H_2O$ | 0.05 | g/dl |
| KCl | 0.03 | g/dl |
| $CaCO_3$ | 0.1 | g/dl |
| (pH 7.0 before sterilization) | | |

Culturing is carried out with aeration and stirring (revolution: 150 r.p.m.; aeration: 80 l/min.) at 30° C for 4 days. Following the procedure of Example 1, about 42 g of the crude Fortimicin complex exhibiting an activity of about 560 unit/mg is obtained. The crude powder is subjected to purification in the same manner as described in Example 1, whereby about 2.4 g of the free base of Fortimicin C exhibiting an activity of about 980 unit/mg is obtained.

EXAMPLE 6

In this example, *Micromonospora olivoasterospora* MK-80, KY 11055 (FERM-P No. 2192, ATCC 31010) is used as a seed strain. The seed strain is cultured in four steps as in Example 1 using a seed medium comprising: 1 g/dl glucose, 1 g/dl soluble starch, 0.5 g/dl yeast extract, 0.5 g/dl peptone and 0.1 g/dl calcium carbonate (pH 7.0 before sterilization). The seed culture liquor from the fourth seed culturing is then inoculated into a main fermentation medium. However, in this example, the fermentation medium of Example 5 is used. From the resulting fermentation liquor, a crude powder of the Fortimicin complex is isolated by the same procedure as described in Example 1. As the result, about 52 g of a crude powder of the Fortimicin complex exhibiting an activity of about 515 unit/mg is obtained. The crude powder of the Fortimicin complex is purified in the same manner as described in Example 1, whereby about 5 g of a purified preparate of the free base of Fortimicin C exhibiting an activity of about 990 unit/mg is obtained.

EXAMPLE 7

In this example, *Micromonospora olivoasterospora* MK-70 (FERM-P No. 1560) (ATCC 21819) is used as a seed strain. This strain is cultured in the same manner as described in Example 1. After the completion of culturing, 150 l of the culture liquor is adjusted to a pH of 2.5 by the addition of concentrated sulfuric acid and stirred for 30 minutes. Thereafter the culture liquor is adjusted to a pH of 7.0 by the addition of 6N sodium hydroxide solution. Then, 15 l of Amberlite IRC-50 ($NH_4^+$ form) is added to the treated culture liquor and the mixture is stirred slowly for 30 minutes. Thereafter, the resin is separated by filtration using a coarse filter cloth. The resin is washed thoroughly with water and packed in a cylindrical column having an inner diameter of 15 cm and a height of 170 cm. Then, 30 l of 0.5N $NH_4OH$ is passed through the column to obtain 7 l of a concentrate containing the Fortimicin complex as antibacterially active fractions. In the concentrate, in addition to Fortimicin C, Fortimicin A and B and several trace components are found. To fractionate the concentrate, it is further concentrated to 500 ml under reduced pressure and finally 49 g of a crude powder of the Fortimicin complex is obtained by freeze-drying. The thus obtained crude powder is suspended in 50 ml of the lower layer of chloroform, methanol and 17% aqueous ammonia (2:1:1) and charged over cellulose powder packed in a cylindrical glass column having an inner diameter of 5 cm and a height of 100 cm. Development is carried out with the same solvent. The eluate is recovered in fractions and the activity of each of the fractions is determined by the paper disc method. The active fractions are subjected to bioautography against *Bacillus subtilis* No. 10707 to determine the active component contained in the fractions. In the cellulose column chromatography, Fortimicin B, A and C are eluted in their order. The fractions containing Fortimicin C are combined and concentrated under reduced pressure to obtain 12.5 g of a crude, amorphous white powder containing Fortimicin C as a main component. This crude powder is then dissolved in about 50 ml of water and the solution is adjusted to a pH of 7.0 with dilute hydrochloric acid. The solution is passed through a cylindrical glass column having an inner diameter of 2 cm and a height of 80 cm previously packed with Bio-Rex 70 ($NH_4^+$ form) (product of Bio-Rad Laboratories, U.S.A.) and the resin is thoroughly washed with water. The Fortimicin complex comtaining Fortimicin C as a main component is adsorbed on the resin and only impurities are eluted with water. Thereafter, elution is carried out with dilute aqueous ammonia (0–0.2N) according to the gradient elution method. The eluate is recovered in fractions and each of the fractions is subjected to paper chromatography to determine the fractions containing Fortimicin C. The thus obtained fractions containing only Fortimicin C are concentrated under reduced pressure and finally by freeze-drying, 10.2 g of pure Fortimicin C in the free base form is obtained as a white amorphous powder which exhibits an activity of 1,000 unit/mg.

Then, 10 g of the thus obtained free base of Fortimicin C is dissolved in a small amount of water. The solution is adjusted to pH 4.5 with 6N $H_2SO_4$ and freeze-dried to obtain 13.3 g of Fortimicin C sulfate as a white amorphous powder. The Fortimicin C sulfate has an activity of 600 unit/mg.

What is claimed is:

1. Fortimicin C, a composition of matter having an antibacterial activity, having the following structural formula:

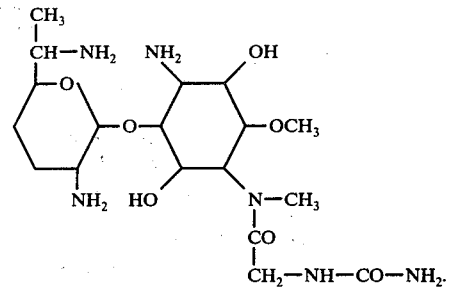

2. A pharmaceutically acceptable acid addition salt of the composition of matter of claim 1, said acid addition salt being selected from the group consisting of the hydrochloride, hydrobromide, hydroiodide, sulfate, sulfamate, phosphate, maleate, acetate, citrate, oxalate, succinate, benzoate, tartrate, fumarate, malate, mandelate and ascorbate.

* * * * *